(12) United States Patent
de Haut et al.

(10) Patent No.: US 6,207,014 B1
(45) Date of Patent: Mar. 27, 2001

(54) SOFTENING LOTION COMPOSITION, USE THEREOF IN PAPER MAKING, AND RESULTING PAPER PRODUCT

(75) Inventors: Christian de Haut, Boissise-le-Roi; Benoit Abribat, Saint-Fargeau-Ponthierry; Maria Da Silva Marques, Vaux-le-Penil; Bruno Bret, Colmar; Jean-Francois Leboeuf, Horbourgwihr, all of (FR)

(73) Assignees: Fort James France, Kunheim; Sidobre Sinnova, Saint-Martory, both of (FR)

( * ) Notice: Subject to any disclaimer, the term of this patent is extended or adjusted under 35 U.S.C. 154(b) by 0 days.

(21) Appl. No.: 09/125,381

(22) PCT Filed: Feb. 10, 1997

(86) PCT No.: PCT/FR97/00255

§ 371 Date: Sep. 10, 1998

§ 102(e) Date: Sep. 10, 1998

(87) PCT Pub. No.: WO97/30216

PCT Pub. Date: Aug. 21, 1997

(30) Foreign Application Priority Data

Feb. 19, 1996 (FR) .................................................. 96 02024

(51) Int. Cl.$^7$ ..................... D21H 17/06; D21H 17/60; D21H 21/24

(52) U.S. Cl. ..................... 162/164.7; 162/172; 162/179; 252/8.63; 252/8.91; 424/401; 428/262

(58) Field of Search ................................. 252/8.63, 8.91; 162/158, 164.7, 172, 179; 428/262; 424/401, 63

(56) References Cited

U.S. PATENT DOCUMENTS

| | | | |
|---|---|---|---|
| 5,871,763 | * 1/1999 | Luu et al. | 424/402 |
| 5,968,530 | * 10/1999 | Arquette | 424/401 |

* cited by examiner

Primary Examiner—Dean T. Nguyen
(74) Attorney, Agent, or Firm—Breiner & Breiner

(57) ABSTRACT

The invention concerns in particular a composition for a softening lotion used in fiber treatment. In the invention, the lotion composition is aqueous and liquid at a temperature of at least 5° C. and comprises, as active substances: (a) one or more saturated linear fatty alcohols having at least 16 carbon atoms, and (b) one or more waxy esters having a total of at least 24 carbon atoms. The application of the invention is to the manufacture of fibrous products such as disposable absorbent paper products.

31 Claims, No Drawings

SOFTENING LOTION COMPOSITION, USE THEREOF IN PAPER MAKING, AND RESULTING PAPER PRODUCT

FIELD OF THE INVENTION

The present invention on the whole concerns a novel composition for a softening lotion used in treating fibers. This lotion is applied on or impregnated into synthetic, artificial, or natural fibers or mixtures thereof, or fibrous structures made in particular from fibers. This lotion, when applied to an absorbent paper product, imparts to the paper a soft slippery feel even though being dry, i.e., not greasy or oily. Furthermore, the invention relates to absorbent paper products treated in this manner.

The invention is applicable to the manufacture of fiber-containing products or structures in the field of papers, non-wovens, textiles and the like.

BACKGROUND OF THE INVENTION

The invention is applicable more especially to the manufacture of paper products such as domestic or sanitary papers. Among these in particular are papers entailing direct contact with the skin and repeated rubbing against the skin, for example disposable paper handkerchiefs, toilet paper or any other paper product for wiping the skin, for removing make-up, dry linen, etc.

People afflicted with colds, influenza or various allergies causing nasal flow will wipe their noses frequently. Oftentimes such people's noses are irritated and red because of skin hypersensitization from this nasal flow. For practical reasons, such people use conventional paper handkerchiefs available commercially in the form of boxed handkerchiefs, also called "facial" tissue, or folded handkerchiefs in small cases. Following several sequential nose wipings with these handkerchiefs, the skin at and around the nose becomes increasingly irritated, even inflamed and painful. Consequently, the surface of these handkerchiefs must be softened in order to limit, even suppress any irritation caused by rubbing the handkerchief surface against the skin. Ideally, the feeling should be the softness offered by a cloth handkerchief that has just been washed and pressed.

In another field, namely that of toilet paper, the same softness is required for repeated contacts with the skin taking place with simultaneous rubbing. In particular as concerns persons suffering from skin irritation in the anal region or in the case of hemorrhoids, a toilet paper with a somewhat rough feel will only further irritate the skin when this paper is pressed against this skin.

Accordingly, endeavors have been underway to generally soften the paper sheets or products, such as the tissue paper webs, using a variety of mechanical or chemical means.

As regards the mechanical means, techniques have been developed to improve in particular the appearance and the surface condition of the paper sheet by endowing it with a more slippery feel. In the case of handkerchiefs illustratively, the sheet is calendered to flatten the crests formed when creping the sheet. Also the sheet surface may be frictionally treated in order to eliminate all roughnesses. However, these approaches often are insufficient. European Patent No. 0 029 269 describes a particular manufacturing procedure for such a sheet wherein the nature of the suspensions of fibers forming the various sheet layers, as well as the combination of these layers among each other, are significant factors for the desired velvety feel. However, this procedure limits the selection of appropriate fibers and entails constraints in the first stages of the wet process phase.

The expression "chemical means" covers any softening composition based on one or several chemical compounds. A distinction may be made between two categories of softening compositions. On one hand, the softening additives or compositions which are directly incorporated into the manufacturing pulp or composition or otherwise are applied to a wet web of paper. And, on the other hand, the softening compositions or lotions which are applied to the surface of a product or a sheet of paper in the dry state, i.e., where prior drying has taken place.

In the first case, these additives as a rule are used as fiber debonding agents and thereby allow flexibilizing of the sheet so made. Many patents have been filed in this field, for example, European Patent Application No. A 0 049 924; European Patent No. B 0 347 176; U.S. Pat. No. 2,944,931; U.S. Pat. No. 5,415,737; and International Application No. WO 95/10661.

European Application No. A 0 049 924 discloses the incorporation of a quaternary ammonium compound and at least one nonionic surfactant selected from fatty acid and fatty alcohol ethylene oxide derivatives into the manufacturing composition in order to achieve a soft absorbent paper. The object of European Patent No. B 0 347 176 is a tissue paper comprising at least one non-cationic surfactant applied to a wet web of paper. However, the surfactant may migrate into the sheet inside and wholly clad the fibers thereby loosening them and decreasing tensile strength. U.S. Pat. No. 2,944,931 discloses a process for improving the softness of toilet paper and its feel consisting in adding a stable aqueous emulsion containing from 1 to 90% by wt. lanolin and from 10 to 99% by wt. of a cationic emulsifier, such as quaternary ammonium salts, to the manufacturing composition. U.S. Pat. No. 5,415,737 concerns a finished soft paper product comprising a vegetal oil-based quaternary ammonium ester compound which is also added to the manufacturing composition. International Application No. WO 95/10661 discloses a manufacturing process for a soft paper with improved feel consisting in added fatty acid ester salts of quaternary amine triethanol as softeners in the fiber aqueous suspensions.

However, on the whole as regards these patents, the product or sheet surface does not offer the desired slippery feature. It is only the product or the web as a whole which is more soft. Moreover, the loss of softening composition during the web manufacturing process is more than trivial.

In the same vein, U.S. Pat. No. 5,279,767 describes more specifically a softening composition comprising a mixture of a quaternary ammonium compound and a polyhydroxy compound. This composition is prepared by mixing in a first stage these two compounds at a high temperature at which they are miscible and then diluting the mixture in high temperature water in order to form an aqueous dispersion of vesicles (or micelles). This composition is preferably incorporated into the manufacturing composition and may be applied to the surface of the formed web, when wet, before drying. It is believed in this patent that the vesicles break up at the time of drying. Most of the polyhydroxy compound so "released" penetrates into the interior of the cellulose fibers and improves the fiber flexibility, the other part being retained at the fiber surface and increases the absorbency rate of fibers. Because of the ionic bonds, the quaternary ammonium compound remains at the surface of the cellulose fibers and thereby the product softness and feel can be improved. This patent does not mention a slippery feel in spite of improved softness. This type of compound addresses an increase in fiber flexibility and it acts substantially within the internal sheet structure, not directly and mainly at the sheet surface.

Variations of this composition are described in other patents such as International Application Nos. WO 94/29,520 and WO 94/29,521.

In the second case, the softening compositions are meant to be applied directly to the product surface or to the absorbent paper sheet surface that was previously dried. Their main function is as a skin emollient.

Many patents illustrate this kind of lotion.

For example, with respect to toilet paper or paper towels used in proctology, U.S. Pat. No. 3,264,188 and French Patent No. 2,376,650 describe lotions providing a fatty feel. The latter patent describes a skin wiping paper product treated with a lipophilic and cleaning emollient, the composition being substantially non-polar and non-aqueous. This emollient may be a mineral oil, petrolatum, paraffin waxes, fatty acids, fatty alcohols, fatty acid esters, derivatives of glycerides, lanolin, polysiloxanes and the like. The emollient settles on the skin surface where it forms a thin film. It allows cleaning of the skin by removing soil. Furthermore, U.S. Pat. No. 4,481,243 has as its object a two ply sheet. An emollient which provides a fatty feel is spread over a large part of the sheet surface. However, the emollient is not applied in a zone where the plies are combined by embossing.

Silicone oils, such as polysiloxanes, may be applied to a tissue paper web in the manner disclosed in European Patent Nos. 0 347 153 and 0 595 994, and in European Patent Application No. 0 656 971. However, some silicone oils are hydrophobic and lower the wettability at the surface of the paper so treated.

The object of U.S. Pat. No. 3,305,392 is a sheet of paper to the surface of which an emollient has been applied by displacing the sheet over a comparatively solid block of an emollient composition similar to wax. This composition comprises a lubricating and softening portion such as zinc stearate; aluminum-, sodium-, calcium- or magnesium-stearate; stearic acid; esters of palmitic or spermacetic acid; stearic alcohol; and where called for additionally esters of stearic and lauric acid polyethylene glycol as effective lubricants. Compounds such as oleic acid, mineral oil, tallow glyceride, distearyl methylamine, primary and secondary fatty amines and derivatives of lanolin, which allow the composition to assume a plastic shape, may also be added. In order to reduce the migration of the compounds inside the sheet, agents may also be provided that contain an active group affixing itself on the cellulose fibers, these agents being cationic. Because this kind of composition is in a fairly solid state, it can be used only at lower speeds and the applied quantities will not be optimized by such techniques.

There are other patents which also relate to lotions which at ambient temperature are solid or semi-solid. U.S. Pat. No. 3,896,807 describes an emollient composition in the form of a non-adhesive and non-oily solid. This composition is heated or admixed with non-aqueous solvents of the type such as acetone, chloroform, trichloroethylene, xylene, xylol and other aromatic solvents in order to be impregnated in liquid form onto a substrate, for example, made of paper. Accordingly, this composition requires for application either heating means or solvents which for the most part for toxicological reasons cannot be used. The main components of this composition are an oil phase containing an oil material, such as mineral oil, petrolatum, paraffin, vegetal oil and different animal oils, and possibly emollients such as cetyl alcohol, propylene glycol, glycerin, triethylene glycol, waxes, and an emulsifier. This kind of lotion is significant because when moisture makes contact with the skin, this composition forms an oil emulsion in water to act as an emollient.

A more recent International Patent Application, namely WO 95/16824, furthermore suggests an anhydrous lotion which is solid or semi-solid at 20° C. but which entails constraints regarding its application to a sheet. This procedure assumes heating means and all the accompanying problems both with respect to the material selected for impregnation and the liquid and stable state of the lotion which in this procedure must remain at a fairly constant temperature.

Some emollients, such as lanolin, incur drawbacks linked to their odor or to the fact they decrease the sheet absorbency. European Patent No. 0 365 726 attempts to remedy these problems by proposing lotions with a single water-soluble component, namely lauroamphoglycinate, quaternary ammonium homo- or copolymeric derivatives, a tri-quaternary phospholipidic complex or a glutamate glucose complex.

French Patent No. 2,538,238 describes a process in which a substrate, for example a strip of paper from which paper towels will be made, passes through a lotion dissolved in an organic solvent and where this solvent then is caused to evaporate. The substrate furthermore may be impregnated practically up to saturation with an aqueous emulsion of which the ingredients are absorbed by the substrate and then dried to completely eliminate the water from the emulsion. The lotion contains a surfactant compound and a fatty body. The two above mentioned procedures entail subsequent evaporation or drying stages that preferably are avoided when manufacturing tissue paper webs.

Once applied, some lotions modify the physical and mechanical properties of the absorbent paper products or of the sheet of paper, such as absorbency, tensile strength in the direction of advance and in the transverse direction, etc. It is especially important that a lotion-impregnated product maintain the best possible strength properties as the same product to which no lotion is applied.

OBJECTS AND BRIEF DESCRIPTION OF THE INVENTION

The object of the invention is to palliate the set of drawbacks met with when using lotions applied to an absorbent paper product both when applying the lotion to a product surface and when the product is used in various ways in wiping skin.

The object of the invention is to provide a lotion composition implementing an especially soft and slippery feel to the fibers, in particular to fibrous structures such as cellulose fiber based absorbent paper products. This allows limiting irritation caused by the paper product rubbing against the skin. Other objects of the invention are to provide a composition imparting greater pliancy and a more velvety feel to the fibrous structures. Moreover, this feel remains dry, contrary to the case of some lotions which once impregnated for example in a paper product provide a greasy feel or deposit a grease film on the skin or on spectacles occasionally wiped by means of this kind of product, handkerchief or facial tissue.

The object of the invention is to provide a lotion composition which is liquid at a temperature of at least 5° C. Preferably the composition is a liquid at a temperature of from about 10 to about 40° C., thereby eliminating any difficulty in applying lotions which are solid or semi-solid at ambient temperature and in general require heating for application to a fibrous surface such as an absorbent paper product.

Another object of the invention is to apply a lotion in small amounts to fiber structures, in particular to the surfaces of paper products.

Another object of the invention is to provide a paper product of which at least one surface has been impregnated with such a lotion, and all resulting paper products.

The physical and mechanical properties of the paper product or the sheet of paper of the invention thusly treated are not significantly modified as regards its thickness or its absorbency or its tensile strength in the direction of advance and in the transverse direction. A sheet comprising the lotion can be advantageously embossed without thereby incurring any problem.

As a rule, the softening lotion composition is meant to treat such natural fibers as cellulose fibers (for example paper, cotton, flax fibers, etc.), artificial fibers (for example viscose fibers) and synthetic fibers (for example polyester, polypropylene fibers, etc.) or their mixtures. The treatment is carried out on the fibers per se or on fibrous structures, that is fiber-based structures whether alone or mixed with non-fibrous components. The fibrous structures can be woven or non-woven, and manufactured by dry or wet processes. They cover, illustratively, textiles, nonwovens, products comprising cellulose fibers bound by a latex, papers, etc.

In the following description, the expression "absorbent paper product" denotes a sheet essentially composed of paper fibers and meant for the manufacture of paper products for sanitary and domestic use or the finished absorbent paper product as such. This sheet of paper can be a tissue paper web or wadded fabric, a sheet of absorbent paper of low specific surface weight for example produced by a through-drying procedure, a sheet made the dry way constituted by paper fibers bound by a thermoplastic binder such as a latex, or a sheet of absorbent paper constituted mostly of paper fibers and of synthetic fibers, or any other equivalent product. Accordingly, the sheet can be creped or not and calendered or not. The sheet is made of one or several plies. Other features relating in particular to the specific surface weight are discussed in the description below.

The object of the invention is a composition for a softening lotion used to treat fibers.

In an essential feature of the invention, the lotion composition is aqueous, liquid at a temperature of at least 5° C., and comprises as active ingredients:

(a) one or more saturated linear fatty alcohols having at least 16 carbon atoms, and (b) one or more waxy esters having a total of at least 24 carbon atoms.

In another feature of the invention, the composition furthermore comprises as an active substance:

(c) one or more nonionic and/or amphoteric emulsifiers.

In one advantageous implementation of the invention, the fatty alcohol(s) comprise(s) from 16 to 28 carbon atoms and the waxy alcohol ester(s) from 24 to 48 carbon atoms.

In another advantageous feature of the invention, the composition comprises from 1 to 50% by wt. of active substances.

In yet another feature of the invention the composition comprises, in weight % of active substances:

(a) 35 to 90% of saturated linear fatty alcohols having 18 to 24 carbon atoms, (b) 1 to 50% of waxy esters having a total of 24 to 48 carbon atoms, (c) 0 to 20% nonionic and/or amphoteric emulsifiers, and (d) 0 to 50% of mineral oil or wax.

The total of the component quantities are about 100% by wt. of active substances.

In a highly advantageous feature of the invention, the component (a) comprises behenic alcohol as the fatty alcohol.

Another object of the invention is a softening lotion having the above composition for treating paper fibers or an absorbent paper product.

In one feature of the invention, an approximate quantity of 0.30 to 20% by wt., and preferably from about 1 to about 10% by wt., of lotion based on the dry weight of an absorbent paper product is applied to the product.

Furthermore, an absorbent paper product is also an object of the invention.

In an essential feature of the invention, at least one surface of the product is impregnated with a softening lotion having an above-defined composition.

In another feature of the invention, at least one surface of the product is impregnated with a softening lotion and this product comprises:

paper fibers, at least one saturated linear fatty alcohol having at least 16 carbon atoms, and at least one synthetic waxy ester derived from a saturated, linear fatty acid, having 10 to 24 carbon atoms and a saturated linear fatty alcohol having 10 to 24 carbon atoms.

In one advantageous feature of the invention, this product is a disposable paper handkerchief.

Other features and advantages of the invention are elucidated in the following description.

DETAILED DESCRIPTION OF THE PRESENTLY PREFERRED EMBODIMENTS OF THE INVENTION

The components used in preparing the lotion are the following. Be it noted that the essential lotion components are emollient in nature.

The component (a) comprises one or more saturated linear fatty acids having at least 16 carbon atoms. In general the component (a) is a mixture of fatty alcohols of which the largest fraction (exceeding 50% by wt.) has chain lengths longer than 16 carbon atoms. Most of the fatty alcohols therefore have chain lengths in excess of 16 carbon atoms, a slight fraction of fatty alcohols possibly comprising fewer. More specifically, the component (a) is a mixture of fatty alcohols having from 16 to 28 carbon atoms and preferably 18 to 24 carbon atoms. In a still more preferred embodiment, the saturated linear fatty alcohols have 22 to 24 carbon atoms. Suitable fatty alcohols are cetyl alcohol, stearyl alcohol, arachyl alcohol, behenic alcohol, lignoceric alcohol and ceryl alcohol. Preferably the component (a) is composed of behenic alcohol. Animal vegetal or natural origin fatty alcohols are selected, allowing the lotion composition containing these compounds together with other suitable constituents to be biodegradable. Illustratively, the fatty alcohols are prepared from vegetal oil by transesterification, distillation, hydrogenation of the esters so prepared and fractionation of the crude fatty alcohols so obtained. These fatty alcohols are denoted being "technical".

The length of the carbon chain of the fatty alcohol is essential with respect to applying the lotion to the surface of fibrous structures. A sufficiently long chain allows this kind of molecule to remain at the surface of the fibrous structure, such as a sheet of paper, rather than penetrating the surface and migrate into the structure.

This observation more particularly relates to the absorbent paper products treated with this lotion.

The component (b) comprises one or more waxy esters having a total of at least 24 carbon atoms. This component (b) also is a mixture of waxy esters of which the largest fraction evinces chain lengths larger than 24. Preferably the waxy esters evince a total of 24 to 48 carbon atoms and are linear and saturated. More preferred yet, the waxy esters have a total of at least 28 carbon atoms. The saturation of the esters allows limiting odor problems relating to some ester compounds. The waxy esters can be natural or synthetic in origin.

The waxy esters are preferably of synthetic origin and derived from saturated, linear fatty acids having 6 to 24 carbon atoms, preferably 10–24 carbon atoms and more preferably 12 to 22 carbon atoms and of saturated, linear fatty alcohols having 6 to 24 carbon atoms, preferably 10 to 24 carbon atoms and more preferably 12 to 22 carbon atoms.

Accordingly, the waxy esters can be prepared from a fatty acid evincing a long chain and a fatty alcohol evincing a shorter chain or vice-versa. Also, the chain lengths of the fatty acid and alcohol can be identical provided that the ester evince a total of at least 24 carbon atoms. Preferably, these esters are prepared from a fatty acid and a fatty alcohol of similar chain, and comparatively long length, namely larger than 14.

Suitable waxy esters are those of lauric, myristic, palmitic, stearic, arachidic, behenic acids with lauric, myristic, cetyl, stearyl, arachyl, behenic alcohols, illustratively decyl stearate, stearyl laurate and behenyl behenilate. Preferably cetyl stearate is used.

The component (c) comprises one or more emulsifiers allowing dispersion of components (a) and (b) in water.

Preferably, the component (c) consists of one or more nonionic and/or amphoteric emulsifiers. These are combinations of nonionic and/or amphoteric surfactants which are distinguished by an alkylaryl, alkylene, alkyl, linear, lipophilic part and at least one hydrophilic group. This hydrophilic function can be just as well an ionic group as an nonionic group.

The nonionic emulsifiers contain hydrophilic groups such as a polyol group, a polyalkyleneglycolether group or a combination of polyols and polyglycolether groups.

Preferably O/W (oil-in-water) type emulsifiers are used that contain at least one of the compounds selected from the group consisting of:

(c1) linear C8–C24 alcohol derivatives, C12–C22 fatty acid, alkyl C8–C15 phenol or alkyl polyol, with 2 to 50 moles of ethylene oxide and/or 0 to 5 moles of propylene oxide, (c2) C6 to C22 unsaturated or saturated fatty acid mono- or di-esters and ethoxylated or not sorbitol or glycerol mono- or di-esters, (c3) C8–C22 alkyl mono- and oligo-glucoside or their ethoxylated analogues, (c4) ricinus oil and ricinus oil hydrogenated with 15 to 60 moles of ethylene oxide, and (c5) polyols, in particular polyglycerol ester such as polyglycerol polyricinoleate or polyglycerol poly-12-hydroxystearate, and/or mixtures of these compounds.

The amphoteric emulsifiers are of the betaine type such as the derivatives of C2 to C18 aminated acid or imidazoline derivatives.

Derivatives of the following compounds can be used as the amphoteric emulsifiers:

N-alkyl-N,N-dimethyl glycinate of ammonium, for example ammonium dimethyl glycinate of copra fatty acid, ammonium N-acyl-aminopropyl-N,N-dimethylglycinate, 2-alkyl-3-carboxymethyl-3-hydroxyethylimidazoline wherein the alkyl chain comprises 8 to 18 carbon atoms, and cocosacylaminoethylhydroxy-ethylcarboxymethylglycinate.

In particular, the derivatives of fatty acid amides known as CFTA cocamidopropylbetaine can be used.

Amphoteric emulsifiers derived from a C8–C18 or acyl alkyl group can be used of which the molecule contains at least one free amine group and a functional group —COOH— or —SO$_3$H—, for example C2–C18 aminated acid derivatives such as N-alkylglycin, N-alkylamino propionate, N-alkylsarcosinate and N-alkyliminodipropionate.

Amphoteric emulsifiers such as N-cocoalkylaminopropionates, cocoacylaminopropionates and acylsarcosinates with C12–C18 are preferred.

Component (c) is optional if, for example, dispersion of the components (a) and (b) in water is carried out mechanically.

The fatty alcohols, waxy esters and emulsifiers are selected in such a way that they will not generate odors in the composition.

Other secondary emollients (fatty alcohols and esters having shorter chains, etc.) can be considered also provided that they do not modify the properties of the aqueous composition.

Where appropriate, secondary additives can be added to the lotion composition. These are conventionally used agents for lotions, creams or any emollient product. Illustratively, they are thickeners, perfumes, vegetal extracts, menthol, eucalyptus, niaouli, and also virucidal and bactericidal compounds. These agents are added in appropriate amounts to the lotion.

Soothing and cicatrizing components for skin irritations, in particular the nose, can be incorporated into the lotion. Illustratively such components are allantoin, certain vegetal extracts, etc.

In weight % of active substances, the lotion composition comprises 35 to 90% of component (a), 1 to 50% of component (b), 0 to 20% of component (c) and 0 to 50% wax or mineral oil (d), the total of the quantities of components (a), (b), (c) and (d) being approximately 100%. Preferably, 1 to 7 and especially 1.5 to 5% by wt. of active substance emulsifier is used.

The lotion composition is aqueous in the form of a dispersion or suspension. Preferably, it will be an aqueous dispersion of the oil-in-water type. The expression "dispersion" is construed broadly, namely as being a mixture of one liquid phase or solid phase in the form of globules or particles in another liquid phase acting as a vehicle. The lotion composition comprises 1 to 50% by wt. of active substances. Specifically, it comprises about 15 to about 45% by wt. active substances and about 55 to 85% by wt. water, and preferably about 20 to about 40% by wt. active substances and about 60 to 80% by wt. water. Part of the water can be substituted by a mineral-origin wax or oil such as paraffin wax or oil. In that case the concentration of mineral-origin wax or oil is approximately 1 to 10% by wt. of active substances. A composition with low levels of water is preferred for treating absorbent paper products.

Whatever the lotion composition defined in the above description, its state shall be liquid at a temperature of at least 5° C. Preferably, the composition is liquid at ambient temperature, that is between about 10 and about 40° C., whereby it can be conventionally applied to a fibrous structure.

The aqueous composition of the invention is biodegradable.

The aqueous dispersion is prepared in a vat equipped with a mixer, a cooling system and a heat exchanger. The mixture so prepared then moves through a homogenizer. The dispersion is chemically and physically stable. It is homogeneous. It is virtually free of separation and thickening. The dispersion viscosity is appropriate for conventional application by atomization or spraying, coating, etc., on the surface of an absorbent paper product. The dispersion is a skin emollient. A compound of the fatty acid alkyl ester is known per se to evince the function of lubricating the skin and eliminating skin moisture losses through evaporation to preclude any skin drying. A compound of the fatty alcohol type is known per se for its function of softening and smoothing the skin surface. The aqueous composition thusly formulated and applied to a fiber, specifically to a fibrous structure such as an absorbent paper product, softens the surface of the fiber or fibrous structure. Its main effect on an absorbent paper product on one hand is to impart a soft and slippery feel to the paper which remains dry, and on the other hand to soften the skin surface in contact with this paper. In the illustrative case of paper handkerchiefs, the softening and emollient composition imparts a noticeably soft feel to the handkerchiefs and considerably reduces irritation incurred by people wiping their noses with conventional handkerchiefs.

Illustrative and more specific compositions are listed below.

| Composition A | Composition B |
| --- | --- |
| (a) C18–C24 saturated linear fatty alcohols | (a) C18–C22 saturated linear fatty alcohols |
| (b) C32 saturated linear waxy esters | (b) C28 saturated linear waxy esters |
| (c) Emulsifier: ethoxylated fatty alcohols | (c) Emulsifier: ethoxylated fatty alcohols |

The lotion composition can be prepared well before it is applied to a fibrous structure and as a result on-site equipment to prepare the composition where it will be industrially applied to the product is unnecessary. The fibrous structures can be treated or impregnated with the lotion in whole or in part.

The following description elucidates the application of the lotion to paper products and, more specifically, a tissue paper web that is converted for the manufacture of paper handkerchiefs.

The tissue paper web to be treated is manufactured by any conventional procedure for making tissue paper. The pulps used are conventional. These pulps can be fresh and of the chemical type and/or they can be bleached in CTMP (chemical-thermomechanical) manner. They can be from hardwood and/or conifers. They can be de-inked pulps from hardwood and/or conifers or their mixtures. The fiber manufacturing composition or aqueous suspension, illustratively, contains a mixture of 60% chemical conifer bleached pulp and 40% chemical bleached eucalyptus pulp. When using recycled fibers, the manufacturing composition for instance contains A 50 to 95% by wt. de-inked pulp. A humid-resistant agent can be incorporated as an additive in the wet manufacturing stage of the sheet. The sheet is creped or not.

As regards making handkerchiefs, the sheet can be calendered or not. The sheet further can be stratified or not. The sheet is composed of one or several plies, preferably two or three plies. The plies can evince the same or different chemical and/or fibrous composition. Illustratively, the plies can be made from different pulps. As regards a three ply handkerchief, the central ply can be made from more economical pulps than the pulps intended for surface plies. These more economical plies illustratively can be bisulfite pulps or pulps bleached in chemical-thermomechanical manner.

A preferred embodiment of handkerchief manufacture consists of making a handkerchief comprising three plies of different natures or compositions. The central ply's essentially fibrous composition is based on long fibers, for example resin-fiber based pulps, preferably from pines and epiceas. A moisture-resistant additive is incorporated into the composition of this ply. If this additive is already present in a certain quantity in each of the other two plies, a larger quantity of this additive shall be incorporated into the central ply. Illustratively, this additive is a moisture-resistant additive of the epichlorohydrin polyamide-type marketed as KYMENE SLX by Hercules Corp. The two other plies are placed one on each side of the central ply and they form the web surfaces. Their fibrous composition is essentially based on short fibers, for example from pulps based on eucalyptus fibers. These plies comprise a softener or debonder. The web so made offers very good wet strength and hence good solidity, in particular, on account of the composition of the central ply. Moreover, it offers improved surface softness because of the selection of chemical and fibrous composition of the other two, outer plies.

The specific surface weight of the sheet ranges approximately from 12 to 65 g/m$^2$. As regards a facial handkerchief, i.e., a facial tissue such as the commercial boxed tissues, the specific surface weight is about 30 to 45 g/m$^2$, and as regards a tissue folded and packaged into a small case, the specific surface weight is about 35 to 65 g/m$^2$.

The lotion is applied to at least one side of the dry tissue paper web, preferably to both outer sides of the sheet. This treatment can be carried out in several stages during sheet manufacture as soon as the sheet has been dried. With respect to a conventional paper-making machine, the treatment can take place directly following the sheet's drying stage on a Yankee cylinder once the sheet has been creped or following the drying stage by through-drying in another manufacturing procedure. At this stage, a single ply is treated on a single side. The treatment furthermore can be carried out during re-spooling when several plies are being combined to form the sheet. One or both sides of the sheet are treated consecutively or simultaneously. The lotion furthermore can be applied during the conversion stage of sheet into a finished product, toilet paper, handkerchief, facial tissue, napkin, etc. In the case of handkerchief manufacture, the two sides of the sheet illustratively are treated just before embossing the edges defining a handkerchief, with the embossing taking place before cutting and folding of the handkerchief (an edge embossing procedure is described in the French Patent 2,698,314) or following embossing and ply combination. The product also may be embossed over all or part of its surface. Again, the finished absorbent paper product can also be treated with the lotion. In surprising manner, it has been noted that after drying the sheet, regardless of the stage of its manufacture or conversion, the lotion-treated/impregnated surfaces of a sheet lend themselves to problem-free embossing. This feature is an advantage relative to the lotions of the prior art, in particular lotions evincing a greasy feel and which cannot be applied to paper surfaces awaiting embossing, and thus prevent embossing.

The lotion is applied to the product or sheet at an amount of from about 0.30 to about 20% by wt. and preferably from about 0.65 to about 15% by wt. (weight of aqueous composition) based on the weight of the dry product (before applying the lotion). Preferably, however, the lotion is applied at an amount of from about 1 to 10% by wt. based on the dry weight of the product or fibers in the case of a cellulose wadding sheet. In other words, a quantity varying from about 0.3 g/m² to about 3 g/m² is applied to each side of the product or sheet.

In an especially preferred manner, and by optimizing the amount of lotion used and the surface softness of the desired product, the lotion is applied in an amount less than approximately 2% by wt. of active ingredients based on the dry product weight. The finished product so treated then contains less than 2% by wt. of active lotion ingredients based on the dry weight of the absorbent paper product.

The lotion can be deposited by different methods such as atomization, coating, printing such as flexography, or any other technique allowing deposition of the lotion on the sheet surface(s).

Atomization is carried out using a system of conventional nozzles. Lotion droplets are projected onto the outer sheet surface. Atomization is further carried out by devices with air mixing or without air and at low pressure or using rotors. This is a simple deposition procedure and the sheet does not make contact with the deposition device. It has been observed that when the deposition is by atomization, and when treating the two outer surfaces of a sheet with three plies, the lotion partly penetrates inside the sheet as far as the inner ply. When using this technique, quantities of about 1.5 to 3 g/m² were applied.

Coating is carried out using a cylinder-screen onto which the lotion is deposited. The cylinder is made to contact one side of the sheet. The two sides of the sheet can be treated simultaneously using one cylinder per side. The lotion can be deposited on all or part of the cylinder surface, for example, in the form of strips. Moreover, variable quantities of lotion can be deposited on parts of the cylinder surface and consequently as such on the side of the sheet. Using such a coating procedure, it has been noted that the lotion does not penetrate into the inside of a three ply sheet as far as the inner ply and does remain well localized on the sheet surface. As a result, it is possible to advantageously reduce the quantities of applied lotion of the invention on each side of the sheet. The quantities applied by the coating technique range from about 0.3 to 2 g/m², and preferably from about 0.5 to about 1.5 g/m², per side. Other appropriate coating techniques also can be considered.

Tests on a pilot machine were carried out using different lotion compositions. A three ply sheet was treated on both sides. Treatment is either by atomization from a rotor-fitted device or by use of a coating cylinder.

Control 0

A tissue paper web comprising three plies each of 18 g/m² is converted into cut handkerchiefs of which the edges are bonded and embossed in the manner described in French Patent No. 2,698,314.

EXAMPLE 1

A composition of the invention in the form of an aqueous dispersion was used. This composition comprises:

| (a) | C18–C24 saturated linear fatty alcohols |
| (b) | C32 saturated linear waxy esters |
| (c) | Emulsifier: ethoxylated fatty alcohols |

This lotion was applied on the pilot machine to a tissue paper web by means of the rotor-fitted device. In the dry state, the tissue paper web to be treated comprising three plies each of 17 g/m² was calendered. The lotion was applied at the amount of 2.5 g/m² per side. The web thusly treated with the Lotion A then was converted into a handkerchief in the manner of the procedure described in French Patent No. 2,698,314.

The same web, but untreated by the lotion, also was converted into a handkerchief by the above procedure and served as Control 1.

EXAMPLE 2

The lotion of which the composition is described in Example 1 was applied to a calendered web comprising three plies each of 20.5 g/m². The treatment was carried out using a coating cylinder. A quantity of 0.6 g/m² was applied to each side of the sheet so that the total applied quantity was comparatively low and hence advantageous. The sheet thusly treated with the lotion was then converted into a handkerchief in the manner described in French Patent No. 2,698,314.

The same web, but untreated by the lotion, also was converted into a handkerchief by the above procedure and was used as Control 2.

The handkerchiefs made in the manner of Examples 1 and 2 and the control handkerchiefs were sense-tested on 40 people.

A series of tests was carried out concerning the parameters of softness, flexibility and thickness. The person testing the product selected a qualifier on a verbal scale. The method consists in giving grades to this verbal scale as shown in the table below by comparing, on one hand, one of the handkerchiefs of one of Examples 1 and 2 and, on the other hand, the control handkerchief corresponding to 1 and 2 with the same Control 0 for a given parameter.

| Verbal Scale/Grade | |
| --- | --- |
| Clearly less | −3 |
| Less | −2 |
| Probably less | −1 |
| The same | 0 |
| Probably more | +1 |
| More | +2 |
| Clearly more | +3 |

The number of persons having selected a particular qualifier was multiplied by the grade of this qualifier. Then the points so obtained were summed and the sum divided by the total number of persons to arrive at an average grade. This average grade falls between −3 and +3, the particular value being the test result. Table I lists the test results. Be it noted that the Controls 1 and 2 without lotion already offer fairly high softness which is inherent in the particular manufacturing procedure of the tissue paper web. Therefore, the softness of the handkerchiefs impregnated with the lotion of the invention was rated relative to a level already acknowledged as being good.

TABLE I

|  | Softness | Flexibility | Thickness |
|---|---|---|---|
| Control 1 | +0.15 | −0.6 | −0.6 |
| Example 1 | +1.2 | +0.2 | −0.45 |
| Difference | 1.05 | +0.8 | +0.15 |
| Control 2 | +0.35 | −0.3 | −0.15 |
| Example | +1.15 | +0.1 | −0.25 |
| Difference | +0.8 | +0.4 | −0.1 |

Test result significance is calculated by the $\chi^2$ method.

The test results of Example 1 and of Control 1 are significant to 1% regarding softness and flexibility.

The test result regarding thickness and Control 1 is significant to 1% and the test result regarding the thickness of Example 1 is significant to 5%.

No significance exists at all for the test results regarding flexibility and thickness concerning Example 2 and its Control.

On the other hand, for the same Example 2 and its Control, the test results are significant to 1% for softness.

Only parameters with significant test results will be discussed. Thickness is considered as being practically unchanged.

Where test results are significant, flexibility is improved.

Lastly, for almost significant test results of Examples 1 and 2, the handkerchiefs were perceived as being softer than the Control handkerchief 0 which per se already is soft.

The difference between an Example and its Control allows evaluating the isolated effect of applying the lotion to the sheet by eliminating the effect of the sheet and of its manufacture.

The best test result (difference between Example and Control) regarding softness is found in Example 1 corresponding to the lotion applied by atomization at a rate of 2.5 g/m² per side.

Still concerning the softness parameter, as regards the applied quantity, the most significant test result is that for Example 2 (difference between Example and its Control), that is, regarding the lotion applied by coating at a rate of 0.6 g/m$_2$ per side.

In general, a clearly improved surface softness is achieved by selecting, as regards the lotion composition, at least one waxy ester having a total of 24 to 48 carbon atoms and by incorporating it in a sufficient amount into the composition so that at least 3% by wt. of active ingredients of this ester relative to the dry weight of the absorbent paper product is present at the surface of the absorbent paper product.

The physical and mechanical properties of the handkerchiefs impregnated in this manner (dry strengths in the direction of advance and in the transverse direction, the elongation in the direction of advance, and the wet strengths in the direction of advance and in the transverse direction) are not significantly modified. They are just as good as those of the Controls. This features represents a substantial advantage.

Absorbencies also have been measured for the handkerchiefs of the set of Examples. Substantial losses in absorbency were expected. In fact such losses were found to be very slight.

Accordingly negative consequences on the physical and mechanical product properties do not arise from treating absorbent paper products with the lotion of the invention.

What is claimed is:

1. Method of using a softening lotion comprising providing a composition comprising as active substances:
    (a) at least one saturated linear fatty alcohol having at least 16 carbon atoms, and
    (b) at least one waxy ester having at least 24 carbon atoms,
   wherein said composition is aqueous and liquid at a temperature of at least 5° C.; and treating paper fibers or an absorbent paper product with said composition which serves as a softening lotion.

2. Method of claim 1, wherein about 0.30 to 20% by wt. of the softening lotion relative to a dry weight of an absorbent paper product is applied to said product.

3. Method of using a softening lotion comprising (i) providing a composition comprising as active substances:
    (a) at least one saturated linear fatty alcohol having at least 16 carbon atoms,
    (b) at least one waxy ester having at least 24 carbon atoms, and
    (c) at least one nonionic and/or amphoteric emulsifier,
   wherein said composition is aqueous and liquid at a temperature of at least 5° C., and
    (ii) treating paper fibers or an absorbent paper product with said composition which serves as a softening lotion.

4. Method of claim 3 wherein about 0.30 to 20% by wt. of the softening lotion relative to a dry weight of an absorbent paper product is applied to said product.

5. Method of using a softening lotion comprising (i) providing a composition comprising, by wt. % of active substances:
    (a) 35 to 90% of at least one saturated linear fatty alcohol having 18 to 24 carbon atoms,
    (b) 1 to 50% of at least one waxy ester having 24 to 48 carbon atoms,
    (c) 0 to 20% of at least one nonionic and/or amphoteric emulsifier, and
    (d) 0 to 50% mineral oil or wax,
   wherein total component amounts are 100% by wt. of said active substances, and wherein said composition is aqueous and liquid at a temperature of at least 5° C., and
    (ii) treating paper fibers or an absorbent paper product with said composition which serves as a softening lotion.

6. Method of claim 5, wherein about 0.30 to 20% by wt. of the softening lotion relative to a dry weight of an absorbent paper product is applied to said product.

7. A composition for a softening lotion for use in treating fibers comprising as active substances:
    (a) at least one saturated linear fatty alcohol having at least 16 carbon atoms, and
    (b) at least one waxy ester having at least 24 carbon atoms,
   wherein said composition is aqueous and liquid at a temperature of at least 5° C.

8. Composition as claimed in claim 7 further comprising s one of said active substances:
    (c) at least one nonionic and/or amphoteric emulsifier.

9. Composition as claimed in claim 7 or 8 wherein said at least one fatty alcohol has from 16 to 28 carbon atoms and said at least one waxy ester has from 24 to 48 carbon atoms.

10. Composition as claimed in claim 7 or 8 wherein said at least one waxy ester is synthetic and derived from saturated linear fatty acids having 6 to 24 carbon atoms and from saturated linear fatty alcohols having 6 to 24 carbon atoms.

11. Composition as claimed in claim 10 wherein said at least one waxy ester is synthetic and derived from saturated linear fatty acids having 10 to 24 carbon atoms and from saturated linear fatty alcohols having 10 to 24 carbon atoms.

12. Composition as claimed in claim 7 or 8 wherein 1 to 50% by wt. of said active substances are present.

13. Composition as claimed in claim 12 wherein 15 to 45% by wt. of said active substances and 55 to 85% by wt. of water are present.

14. Composition as claimed in claim 12 wherein 20 to 40% by wt. of said active substances and 60 to 80% by wt. of water are present.

15. Composition as claimed in claim 7, or 8 wherein component (a) comprises behenic alcohol as the at least one fatty alcohol.

16. Composition as claimed in claim 8 wherein said at least one nonionic emulsifier is selected from the group consisting of derivatives of ethylene oxide and fatty alcohols; fatty acids; alkyl phenols or alkyl polyols; alkyl and/or alkenyl oligoglucosides; polyol esters; mono- or di-esters of fatty acids and of glycerol or sorbitol, ethoxylated or not; derived from ricinus oil and ethylene oxide; and/or mixtures thereof.

17. Composition as claimed in claim 8 wherein the at least one amphoteric emulsifier is a betaine.

18. Composition as claimed in claim 8 wherein said at least one amphoteric emulsifier is a derivative of imidazoline or aminated acids having 2 to 8 carbon atoms.

19. An additive for an absorbent paper product comprising a composition comprising as active substances:
(a) at least one saturated linear fatty alcohol having at least 16 carbon atoms, and
(b) at least one waxy ester having at least 24 carbon atoms,
wherein said composition is aqueous and liquid at a temperature of at least 5° C.

20. An additive for an absorbent paper product comprising a composition comprising as active substances:
(a) at least one saturated linear fatty alcohol having at least 16 carbon atoms,
(b) at least one waxy ester having at least 24 carbon atoms, and
(c) at least one nonionic and/or amphoteric emulsifier,
wherein said composition is aqueous and liquid at a temperature of at least 5° C.

21. An additive for an absorbent paper product comprising a composition comprising, by wt. % of active substances:
(a) 35 to 90% of at least one saturated linear fatty alcohol having 18 to 24 carbon atoms,
(b) 1 to 50% of at least one waxy ester having 24 to 48 carbon atoms,
(c) 0 to 20% of at least one nonionic and/or amphoteric emulsifier, and
(d) 0 to 50% mineral oil or wax,
wherein total component amounts are 100% by wt. of said active substances, and wherein said composition is aqueous and liquid at a temperature of at least 5° C.

22. Composition for a softening lotion for use in treating fibers comprising, by wt. % of active substances:
(a) 35 to 90% of at least one saturated linear fatty alcohol having 18 to 24 carbon atoms,
(b) 1 to 50% of at least one waxy ester having 24 to 48 carbon atoms,
(c) 0 to 20% of at least one nonionic and/or amphoteric emulsifier, and
(d) 0 to 50% mineral oil or wax,
wherein total component amounts are 100% by wt. of said active substances, and wherein said composition is aqueous and liquid at a temperature of at least 5° C.

23. Composition as claimed in claim 22 wherein component (a) comprises behenic alcohol as the at least one fatty alcohol.

24. Composition as claimed in claim 22 wherein said at least one nonionic emulsifier is selected from the group consisting of derivatives of ethylene oxide and fatty alcohols; fatty acids; alkyl phenols or alkyl polyols; alkyl and/or alkenyl oligoglucosides; polyol esters; mono- or di-esters of fatty acids and of glycerol or sorbitol, ethoxylated or not; derived from ricinus oil and ethylene oxide; and/or mixtures thereof.

25. Composition as claimed in claim 22 wherein the at least one amphoteric emulsifier is a betaine.

26. Composition as claimed in claim 22 wherein said at least one amphoteric emulsifier is a derivative of imidazoline or aminated acids having 2 to 8 carbon atoms.

27. An absorbent paper product having at least one surface of said product impregnated with a softening lotion of a composition comprising as active substances:
(a) at least one saturated linear fatty alcohol having at least 16 carbon atoms, and
(b) at least one waxy ester having at least 24 carbon atoms,
wherein said composition is aqueous and liquid at a temperature of at least 5° C.

28. Absorbent paper product having at least one product surface impregnated with a softening lotion, said paper product comprising
paper fibers,
at least one saturated linear fatty alcohol having at least 16 carbon atoms, and
at least one synthetic waxy ester derived from a saturated linear fatty acid having 10 to 24 carbon atoms and from a saturated linear fatty alcohol having 10 to 24 carbon atoms.

29. Product as claimed in claim 28 wherein said paper product is a disposable paper handkerchief.

30. An absorbent paper product having at least one surface of said product impregnated with a softening lotion of a composition comprising as active substances:
(a) at least one saturated linear fatty alcohol having at least 16 carbon atoms,
(b) at least one waxy ester having at least 24 carbon atoms, and
(c) at least one nonionic and/or amphoteric emulsifier,
wherein said composition is aqueous and liquid at a temperature of at least 5° C.

31. An absorbent paper product having at least one surface of said product impregnated with a softening lotion of a composition comprising, by wt. % of active substances:
(a) 35 to 90% of at least one saturated linear fatty alcohol having 18 to 24 carbon atoms,
(b) 1 to 50% of at least one waxy ester having 24 to 48 carbon atoms,
(c) 0 to 20% of at least one nonionic and/or amphoteric emulsifier, and
(d) 0 to 50% mineral oil or wax,
wherein total component amounts are 100% by wt. of said active substances, and wherein said composition is aqueous and liquid at a temperature of at least 5° C.

* * * * *